United States Patent
Jiang et al.

(10) Patent No.: US 8,435,271 B2
(45) Date of Patent: May 7, 2013

(54) DEVICE FOR FIXING SOFT TISSUE

(75) Inventors: Ching-Chuan Jiang, Taipei (TW);
Shan-Chang Chueh, Taipei (TW);
Ting-Hui Chiu, Hsinchu County (TW);
Chun-Jen Liao, Taipei (TW); Yi-Hung Lin, Hsinchu County (TW); Ya-Jen Yu, Taipei (TW); I-Fan Chiu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/231,924

(22) Filed: Sep. 13, 2011

(65) Prior Publication Data

US 2012/0004675 A1 Jan. 5, 2012

Related U.S. Application Data

(62) Division of application No. 11/614,033, filed on Dec. 20, 2006, now Pat. No. 8,043, 347.

(60) Provisional application No. 60/755,612, filed on Dec. 29, 2005.

(51) Int. Cl.
*A61B 17/03* (2006.01)

(52) U.S. Cl.
USPC .......................................................... 606/311

(58) Field of Classification Search ............... 606/232, 606/300–331; 623/13.11–13.14
See application file for complete search history.

(56) References Cited

U.S. PATENT DOCUMENTS

| | | | |
|---|---|---|---|
| 4,632,100 A | 12/1986 | Somers et al. | |
| 5,013,316 A * | 5/1991 | Goble et al. | 606/916 |
| 5,100,417 A | 3/1992 | Cerier et al. | |
| 5,141,520 A | 8/1992 | Goble et al. | |
| 5,156,616 A | 10/1992 | Meadows et al. | |
| 5,324,308 A | 6/1994 | Pierce | |
| 5,545,180 A | 8/1996 | Le et al. | |
| 5,741,282 A | 4/1998 | Anspach et al. | |
| 5,851,219 A | 12/1998 | Goble et al. | |
| 5,935,129 A * | 8/1999 | McDevitt et al. | 606/232 |
| 5,989,255 A | 11/1999 | Pepper et al. | |
| 6,117,162 A | 9/2000 | Schmieding et al. | |
| 6,123,711 A * | 9/2000 | Winters | 606/304 |
| 6,383,187 B2 | 5/2002 | Tormala et al. | |
| 6,471,707 B1 * | 10/2002 | Miller et al. | 606/916 |
| 6,692,516 B2 | 2/2004 | West, Jr. et al. | |
| 6,951,561 B2 * | 10/2005 | Warren et al. | 606/328 |
| 7,074,203 B1 * | 7/2006 | Johanson et al. | 602/72 |
| 7,175,625 B2 * | 2/2007 | Culbert | 606/326 |
| 8,043,347 B2 * | 10/2011 | Jiang et al. | 606/311 |
| 2001/0051807 A1 | 12/2001 | Grafton | |
| 2003/0105465 A1 | 6/2003 | Schmieding et al. | |
| 2003/0187447 A1 | 10/2003 | Ferrante et al. | |
| 2004/0133207 A1 * | 7/2004 | Abdou | 606/73 |
| 2004/0181234 A1 * | 9/2004 | McDevitt et al. | 606/104 |
| 2006/0004364 A1 * | 1/2006 | Green et al. | 606/72 |
| 2006/0235410 A1 * | 10/2006 | Ralph et al. | 606/72 |

FOREIGN PATENT DOCUMENTS

TW M 249628 11/2004

* cited by examiner

FOREIGN PATENT DOCUMENTS

*Primary Examiner* — Kevin T Truong
*Assistant Examiner* — Christopher Beccia

(57) ABSTRACT

A device for fixing soft tissue. A sleeve is detachably connected to a self-drilling tapping screw, moving and rotating the self-drilling tapping screw. A guide bar is detachably connected to the self-drilling tapping screw and fit in the sleeve. A fixing pin is fit in a washer and connected to the self-drilling tapping screw. The guide bar is detachably fit in the fixing pin. The fixing pin abuts the washer and the self-drilling tapping screw.

21 Claims, 20 Drawing Sheets

DEVICE FOR FIXING SOFT TISSUE

CROSS REFERENCE TO RELATED APPLICATIONS

This present application is a division of application Ser. No. 11/614,033, filed Dec. 20, 2006, the entirety of which is incorporated by reference herein.

BACKGROUND

1. Technical Field

The invention relates to a device for fixing soft tissue, and more particularly to a device for affixing glenoidal labrum to a shoulder joint.

2. Related Art

A shoulder joint is mainly composed of a ball-like humeral head and a glenoidal cup of scapula, tightly covered by various fibered connective tissues and muscles, performing flexion, extension, adduction, abduction, rotation and circumduction. Moreover, a glenoidal labrum is formed on the edge of the glenoidal cup of the shoulder joint, increasing the surface area of the glenoidal cup, enhancing stability of the shoulder joint, and providing attachment for ligaments.

Operating frequently, the shoulder joint is easily injured or dislocated. Soft tissue, such as ligaments, tendons and cartilage, of the shoulder joint is easily separated therefrom due to sport injury, overuse, or improper posture. Injury to the shoulder joint often includes tearing of tendons of rotator cuff muscles, SLAP (Superior Lesion, Anterior to Posterior, wherein the upper part of the glenoidal labrum is pulled off the glenoidal cup by tendons of biceps of humerus), and Bankart lesion (the lower part of the glenoidal labrum is separated from the glenoidal cup by dislocation of the humerus and drag of the ligament).

The soft tissue of the shoulder joint requires surgical intervention when seriously separated therefrom, such intervention comprising open and arthroscopic techniques. In both cases, suturing directly or indirectly secures the torn or separated soft tissue to the bones of the shoulder joint. For example, torn rotator cuff tendons are attached to the humerus or separated glenoidal labrum to glenoidal cup of the shoulder joint by such suturing.

In a direct fixation method, the soft tissue is directly sutured to bones with drilled holes. Specifically, the soft tissue is fixed to the bones by seaming the sutures between the soft tissue and the holes. This direct fixation method, however, is very time consuming and requires a high degree of surgical precision. Moreover, the sutures are easily broken, adversely affecting reconstruction and regeneration of the soft tissue.

In an indirect fixation method, the soft tissue is fixed to bones by soft tissue anchors. Specifically, the soft tissue anchors are disposed in the bones and the soft tissue is then fixed to both the soft tissue anchors and bones by sutures. There are two types of conventional soft tissue anchor, push-in and turn-in. The push-in soft tissue anchor may comprise ridges, barbs, or extending wings or fingers. When employed, the push-in anchor is inserted into the bones and the ridges, barbs, or extending wings or fingers thereof engage the bones, as disclosed as a suture anchor with annular ridges in U.S. Pat. No. 5,100,417, a harpoon suture anchor with barbs in U.S. Pat. No. 5,141,520, an umbrella-shaped suture anchor device with outwardly extending wing members in U.S. Pat. No. 5,545,180, and a knotless suture anchor with extended fingers in U.S. Pat. No. 6,692,516. The turn-in soft tissue anchor may comprise a tip and threads. When employed, the tip and threads thereof are inserted into the bones, as disclosed in U.S. Pat. No. 4,632,100, U.S. Pat. No. 5,156,616, U.S. Pat. No. 5,851,219, and U.S. Pat. No. 6,117,162.

Accordingly, conventional soft tissue anchors require sutures to pass through eyelets or apertures thereof and to be knotted to secure the soft tissue to bones, complicating surgery. Moreover, when conventional soft tissue anchors are employed in arthroscopic surgery, such for fixing SLAP, operation thereof is very difficult due to limited space. Thus, attaching the separated glenoidal labrum to the glenoidal cup of the shoulder joint by the conventional soft tissue anchors is difficult and time-consuming.

SUMMARY

A detailed description is given in the following embodiments with reference to the accompanying drawings.

A device for fixing soft tissue is disclosed, comprising a self-drilling tapping screw, a sleeve, a guide bar, a washer, and a fixing pin. The sleeve is detachably connected to the self-drilling tapping screw, moving and rotating the self-drilling tapping screw. The guide bar is detachably connected to the self-drilling tapping screw and fit in the sleeve. The fixing pin is fit in the washer and connected to the self-drilling tapping screw. The guide bar is detachably fit in the fixing pin. The fixing pin abuts the washer and the self-drilling tapping screw.

The self-drilling tapping screw comprises a main body and a first threaded portion formed on the outer surface thereof.

The self-drilling tapping screw further comprises a first connecting portion connected to the main body. The sleeve comprises a second connecting portion detachably connected to the first connecting portion.

The first and second connecting portions are complementary.

The self-drilling tapping screw further comprises a central hole formed in the main body. The guide bar is detachably disposed in the central hole.

The central hole comprises a second threaded portion. The guide bar comprises a third threaded portion engaging the second threaded portion.

The self-drilling tapping screw further comprises a central hole formed in the main body. The fixing pin is disposed in the central hole.

The central hole comprises at least one first engaging portion. The fixing pin comprises at least one second engaging portion engaging the first engaging portion.

The first and second engaging portions are complementary.

The central hole comprises a fourth threaded portion. The fixing pin comprises a fifth threaded portion engaging the fourth threaded portion.

The sleeve comprises a first central through hole in which the guide bar is detachably fit.

The device further comprises an anti-slip screw detachably fit in the sleeve and movably protruding into the first central through hole, abutting and fixing the guide bar.

The washer comprises at least one protruding splinter formed on the circumference thereof.

The washer further comprises a second central through hole in which the fixing pin is fit.

The fixing pin further comprises a third central through hole in which the guide bar is detachably fit.

The fixing pin further comprises a retardant portion abutting the washer.

The self-drilling tapping screw, washer, and fixing pin comprise titanium alloy, stainless steel, or biocompatible material.

The washer and fixing pin comprise bio-absorbable macromolecular material.

The washer and fixing pin comprise poly lactide-glycolic acid (PLGA).

A method for fixing soft tissue is disclosed. The method comprises providing a self-drilling tapping screw, connecting a guide bar to the self-drilling tapping screw, fitting a sleeve on the guide bar and moving the sleeve along the guide bar to connect with the self-drilling tapping screw, moving and rotating the sleeve, enabling the self-drilling tapping screw connected thereto to sequentially penetrate the soft tissue and a compact bone and enter a cancellous bone, separating the sleeve from the self-drilling tapping screw and removing the sleeve from the compact bone and soft tissue, fitting a washer on the guide bar and moving the washer along the guide bar to the soft tissue, fitting a fixing pin on the guide bar and moving the fixing pin into the self-drilling tapping screw along the guide bar and through the soft tissue and compact bone, wherein the fixing pin is engaged in the self-drilling tapping screw and abuts the washer and the self-drilling tapping screw, tightly attaching the soft tissue to the compact bone, and separating the guide bar from the self-drilling tapping screw and removing the guide bar from the compact bone and soft tissue.

The method further comprises detachably fitting an anti-slip screw in the sleeve to abut and fix the guide bar.

The method further comprises forcing the washer into the soft tissue, tightly attaching the soft tissue to the compact bone.

BRIEF DESCRIPTION OF DRAWINGS

The invention can be more fully understood by reading the subsequent detailed description and examples with references made to the accompanying drawings, wherein.

DETAILED DESCRIPTION

The following description is of the best-contemplated mode of carrying out the invention. This description is made for the purpose of illustrating the general principles of the invention and should not be taken in a limiting sense. The scope of the invention is best determined by reference to the appended claims.

First Embodiment

Figure 1:
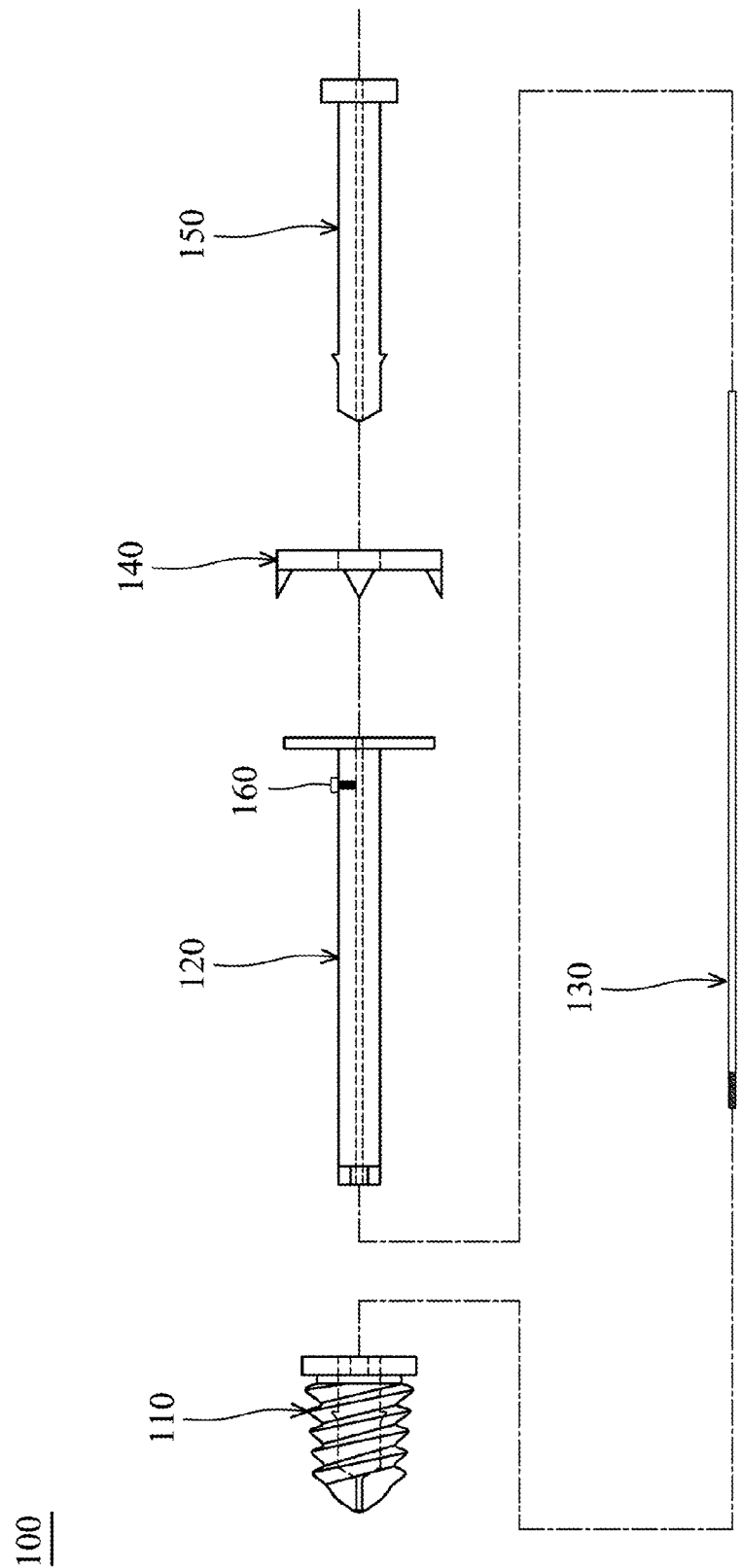
FIG. 1 is a schematic exploded view of a device for fixing soft tissue of a first embodiment of the invention.

Referring to FIG. 1, a device 100 for fixing soft tissue comprise a self-drilling tapping screw 110, a sleeve 120, a guide bar 130, a washer 140, a fixing pin 150, and an anti-slip screw 160.

Figure 2:
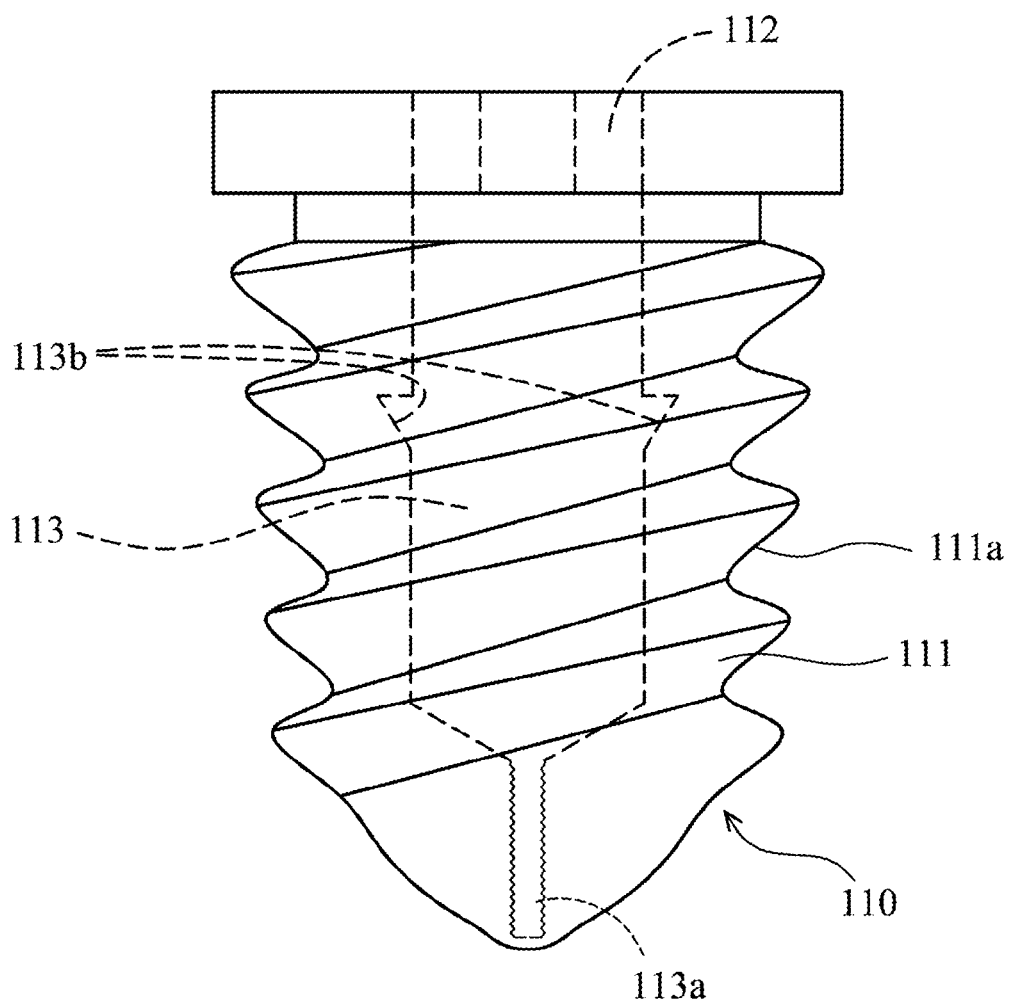
FIG. 2 is a schematic plane view of a self-drilling tapping screw of the device for fixing soft tissue of the first embodiment of the invention.

Referring to FIG. 2, the self-drilling tapping screw 110 comprises a main body 111, a first connecting portion 112, and a central hole 113. The main body 111 comprises a first threaded portion 111a formed on the outer surface thereof. In this embodiment, the first threaded portion 111a is configured with outer threads. The first connecting portion 112 is connected to the main body 111. The central hole 113 is formed in the main body 111 and comprises a second threaded portion 113a and a plurality of first engaging portions 113b. In this embodiment, the second threaded portion 113a is configured with inner threads, and the self-drilling tapping screw 110 may comprise titanium alloy, stainless steel, or biocompatible material.

Figure 3:
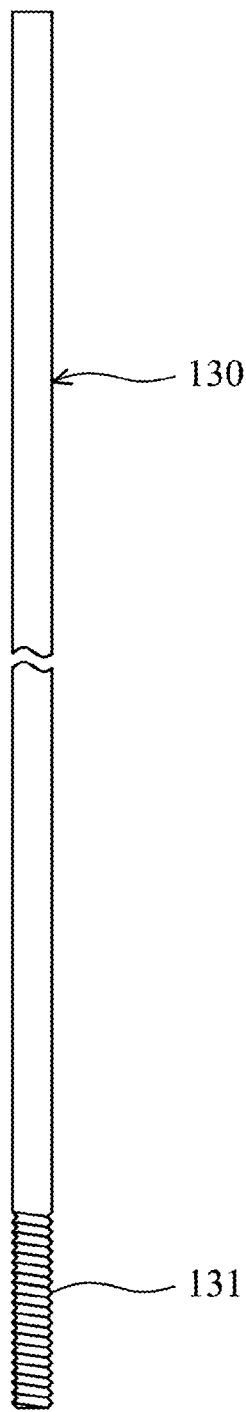
FIG. 3 is a schematic plane view of a guide bar of the device for fixing soft tissue of the first embodiment of the invention.

Referring to FIG. 3, the guide bar 130 comprises a third threaded portion 131. In this embodiment, the third threaded portion 131 is configured with outer threads.

Figure 4:
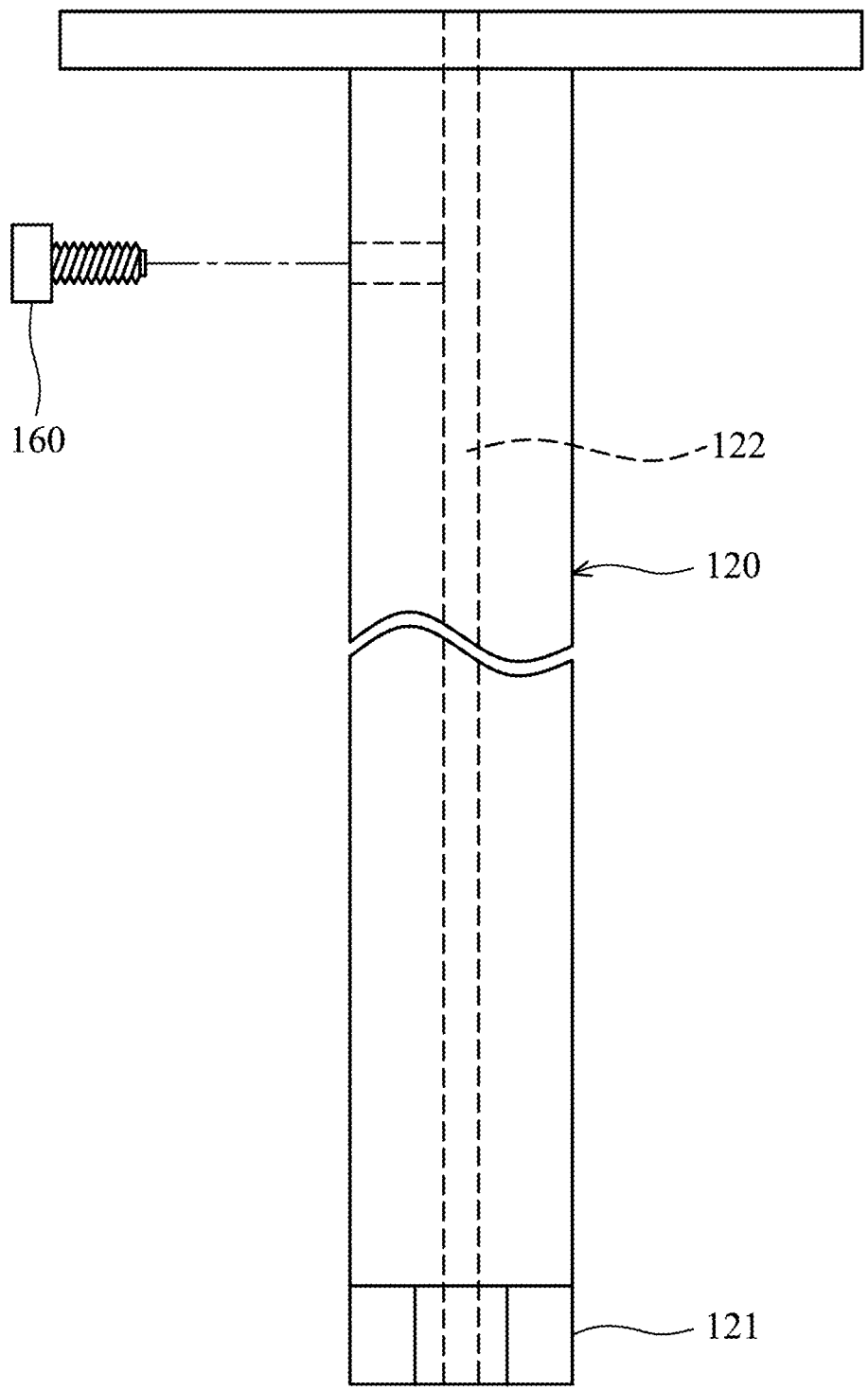
FIG. 4 is a schematic plane view of a sleeve of the device for fixing soft tissue of the first embodiment of the invention.

Referring to FIG. 4, the sleeve 120 comprises a second connecting portion 121 and a first central through hole 122. Specifically, the first connecting portion 112 of the self-drilling tapping screw 110 is complementary to the second connecting portion 121 of the sleeve 120. For example, the first connecting portion 112 may be configured with an inner octagonal profile and the second connecting portion 121 with an outer octagonal profile.

Figure 5:
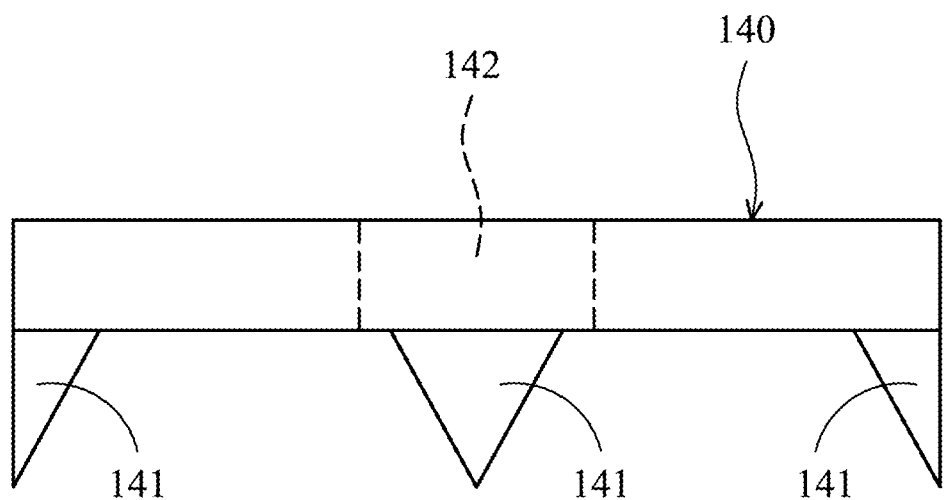
FIG. 5 is a schematic plane view of a washer of the device for fixing soft tissue of the first embodiment of the invention.

Referring to FIG. 5, the washer 140 comprises a plurality of protruding splinters 141 and a second central through hole 142. The protruding splinters 141 are formed on the circumference of the washer 140.

Figure 6:
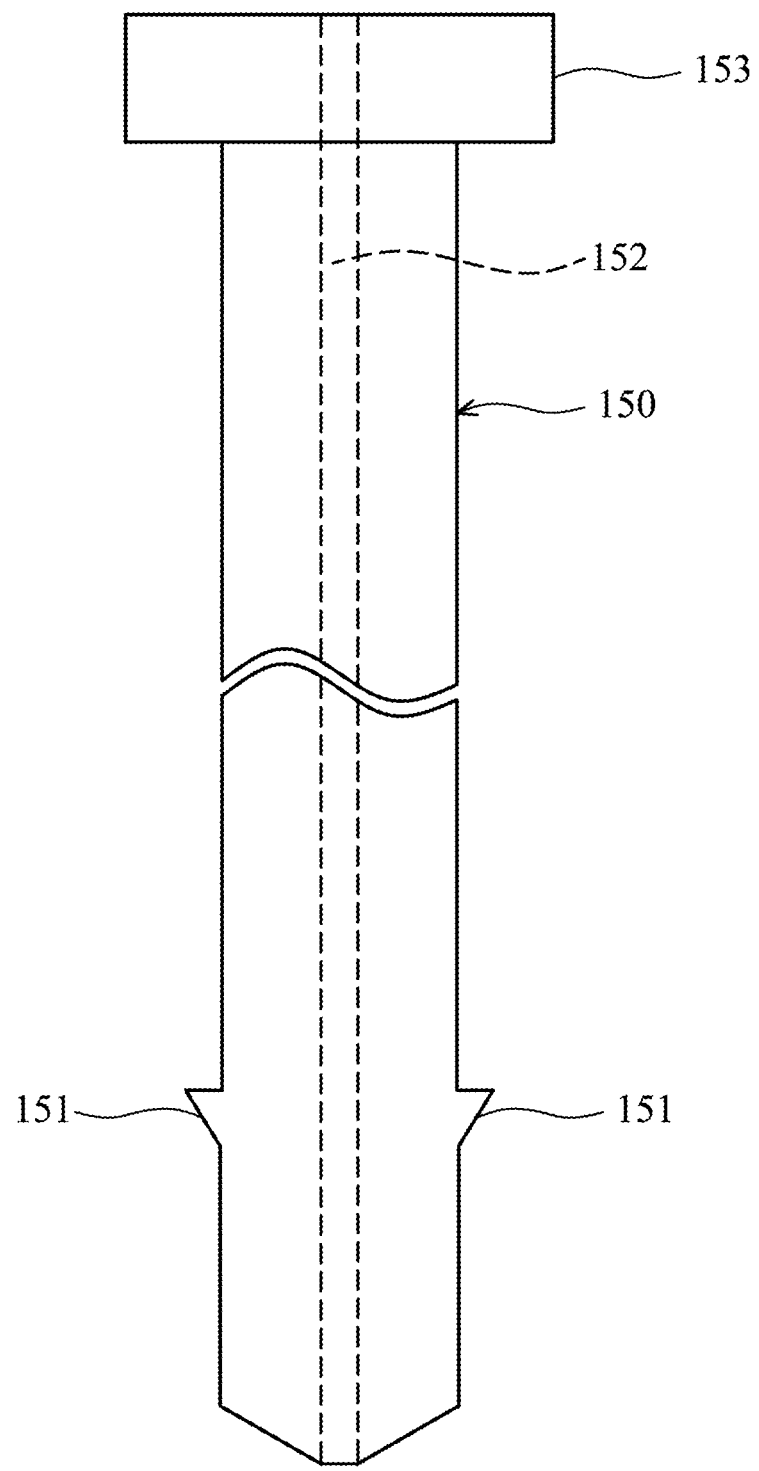
FIG. 6 is a schematic plane view of a fixing pin of the device for fixing soft tissue of the first embodiment of the invention.

Referring to FIG. 6, the fixing pin 150 comprises a plurality of second engaging portions 151, a third central through hole 152, and a retardant portion 153. Specifically, the second engaging portions 151 correspond to and are complementary to the first engaging portions 113b of the central hole 113 in the self-drilling tapping screw 110, respectively. Moreover, the washer 140 and fixing pin 150 may comprise bio-absorbable macromolecular material, such as poly lactide-glycolic acid (PLGA). Additionally, the washer 140 may be integrally formed with the fixing pin 150.

As shown in FIG. 4, the anti-slip screw 160 is detachably fit in the sleeve 120. Specifically, the anti-slip screw 160 moves in the sleeve 120 and protrudes into the first central through hole 122 of the sleeve 120, abutting and fixing the guide bar 130 fit in the first central through hole 122.

The following description is directed to a method for fixing soft tissue using the aforementioned device 100. For example, a separated glenoidal labrum is fixed to a glenoidal cup of a shoulder joint.

Figure 7A:
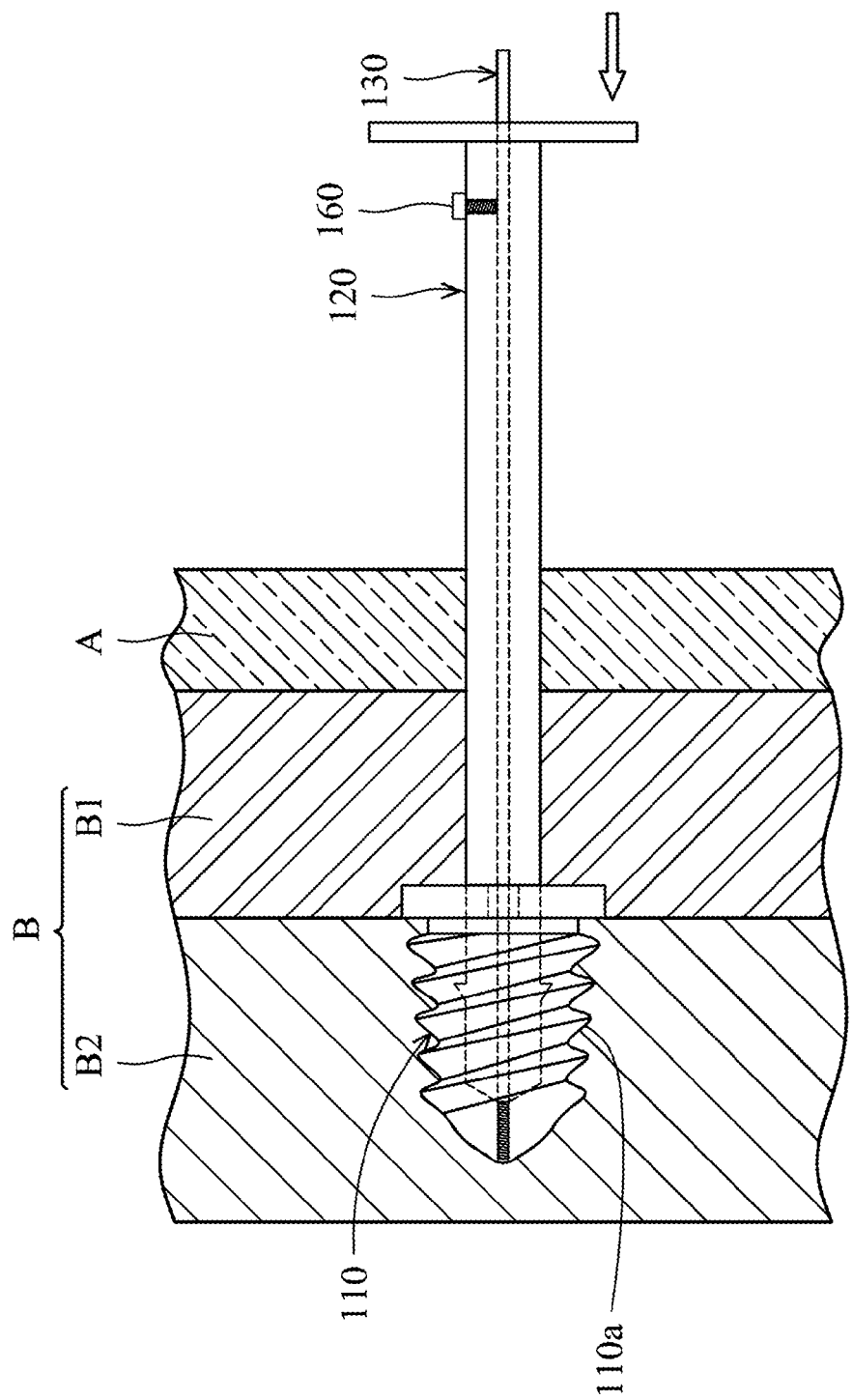
FIG. 7A is a schematic view showing operation of the device for fixing soft tissue of the first embodiment of the invention.

As shown in FIG. 7A, the guide bar 130 is connected to the self-drilling tapping screw 110. Namely, the third threaded portion 131 of the guide bar 130 is engaged with the second threaded portion 113a of the central hole 113 in the self-drilling tapping screw 110. The sleeve 120 is then fit on the guide bar 130 and slides to connect with the self-drilling tapping screw 110 along the guide bar 130. At this point, the guide bar 130 is fit in the self-drilling tapping screw 110 and first central through hole 122 of the sleeve 120, and the second connecting portion 121 of the sleeve 120 engages the first connecting portion 112 of the self-drilling tapping screw 110. The anti-slip screw 160 is fit in the sleeve 120 to abut and fix the guide bar 130, preventing the guide bar 130 from separating from the self-drilling tapping screw 110 or deviating from the central axis of the sleeve 120. The sleeve 120 is moved and rotated toward the glenoidal labrum (soft tissue) A and bones B beneath the glenoidal cup by a simple tool, such as a hammer. As the second connecting portion 121 of the sleeve 120 engages the first connecting portion 112 of the self-drilling tapping screw 110, the self-drilling tapping screw 110 is moved and rotated and sequentially penetrates the glenoidal labrum A and a compact bone B1 of the bones B, thereby entering a cancellous bone B2 of the bones B. As this point, the self-drilling tapping screw 110 is tightly fixed in the cancellous bone B2 by the first threaded portion 111a formed on the main body 111 thereof.

Figure 7B:
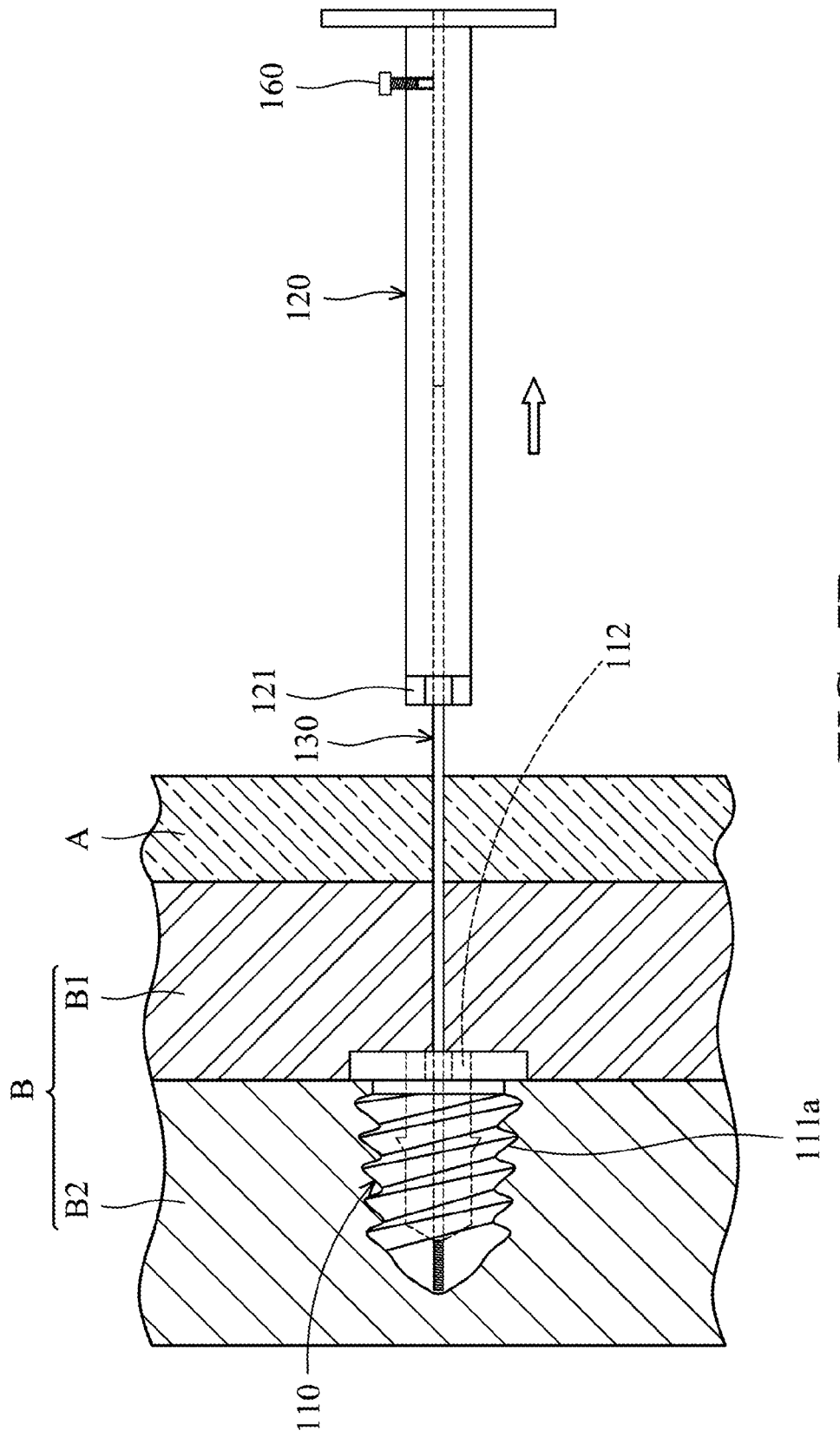
FIG. 7B is another schematic view showing operation of the device for fixing soft tissue of the first embodiment of the invention.

As shown in FIG. 7B, after being loosened, the anti-slip screw 160 is separated from the guide bar 130. The sleeve 120 is separated from the self-drilling tapping screw 110 and guide bar 130. Namely, the second connecting portion 121 of the sleeve 120 is separated from the first connecting portion 112 of the self-drilling tapping screw 110. The sleeve 120 is then removed from the compact bone B1 and glenoidal labrum A.

Figure 7C:
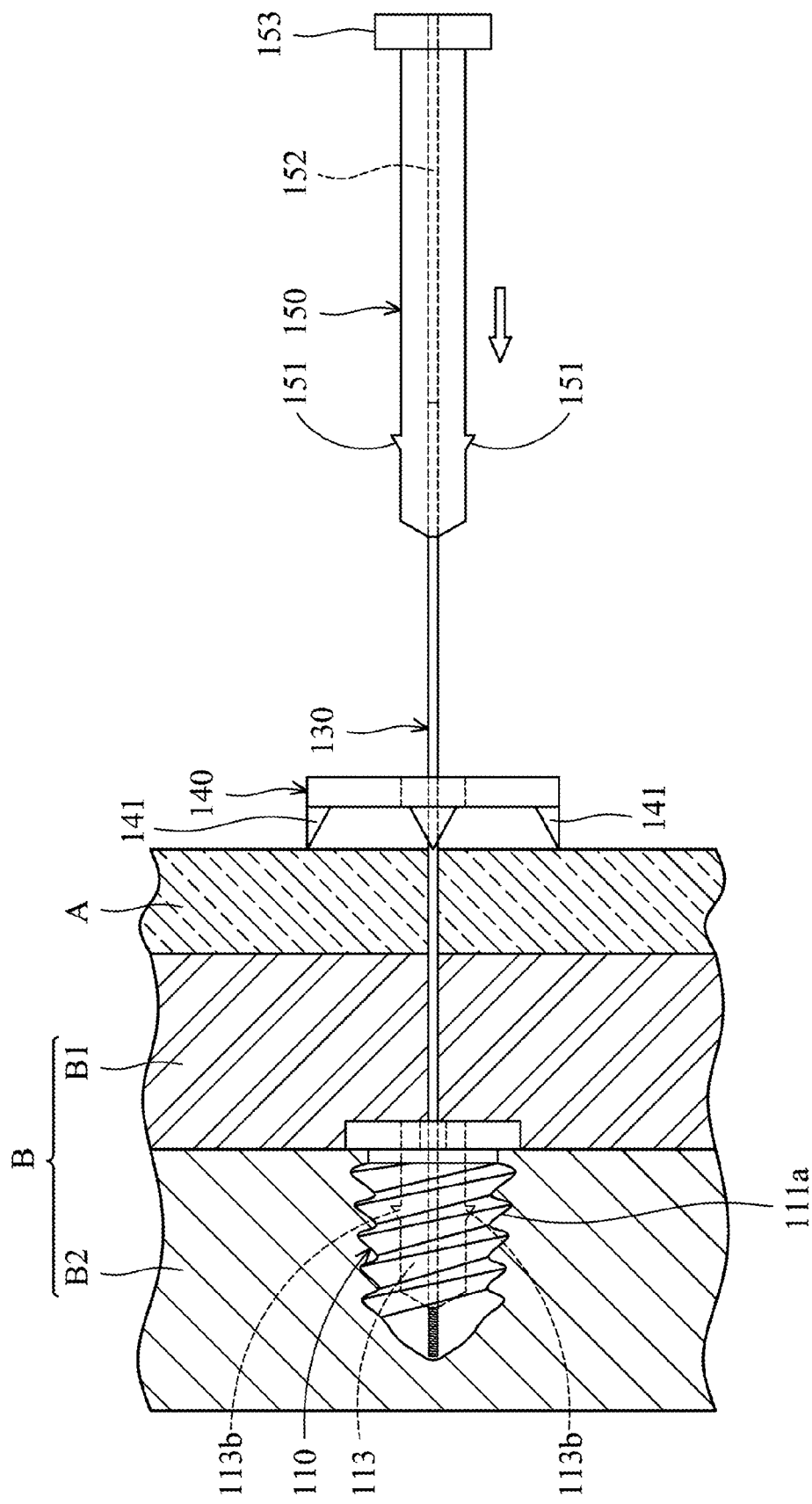
FIG. 7C is yet another schematic view showing operation of the device for fixing soft tissue of the first embodiment of the invention.

As shown in FIG. 7C, the washer 140 is fit on the guide bar 130 and slides to the glenoidal labrum A along the guide bar 130.

Figure 7D:
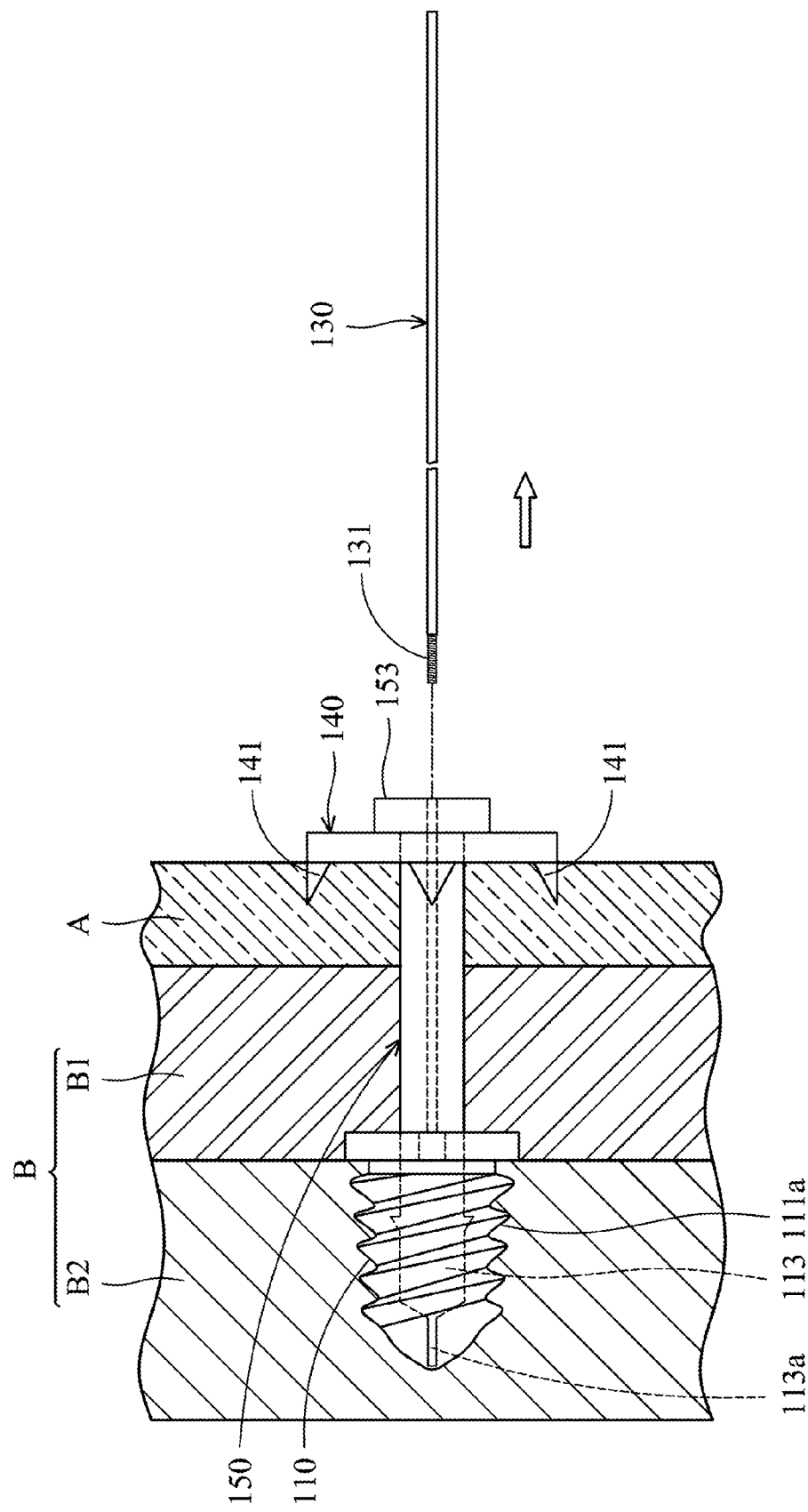
FIG. 7D is still another schematic view showing operation of the device for fixing soft tissue of the first embodiment of the invention.

As shown in FIG. 7C and FIG. 7D, the fixing pin 150 is fit on the guide bar 130 and moved into the self-drilling tapping screw 110 along the guide bar 130 and through the second central through hole 142 of the washer 140, glenoidal labrum A, and compact bone B1. At this point, the second engaging portions 151 of the fixing pin 150 respectively engage the first engaging portions 113b of the central hole 113 in the self-drilling tapping screw 110, the guide bar 130 is fit in the third central through hole 152 of the fixing pin 150, and the retardant portion 153 of the fixing pin 150 abuts the washer 140. Accordingly, the fixing pin 150 abuts the washer 140 and the self-drilling tapping screw 110, thereby attaching the glenoidal labrum A to the compact bone B1.

As shown in FIG. 7D, the guide bar 130 is separated from the self-drilling tapping screw 110. Namely, the third threaded portion 131 of the guide bar 130 is disengaged from the second threaded portion 113a of the central hole 113 in the self-drilling tapping screw 110. The guide bar 130 is then removed to the exterior of the glenoidal labrum A. The washer 140 is pushed into the glenoidal labrum A. At this point, the protruding splinters 141 of the washer 140 are engaged with the glenoidal labrum A, such that the glenoidal labrum A is tightly attached or fixed to the compact bone B1.

Figure 8:
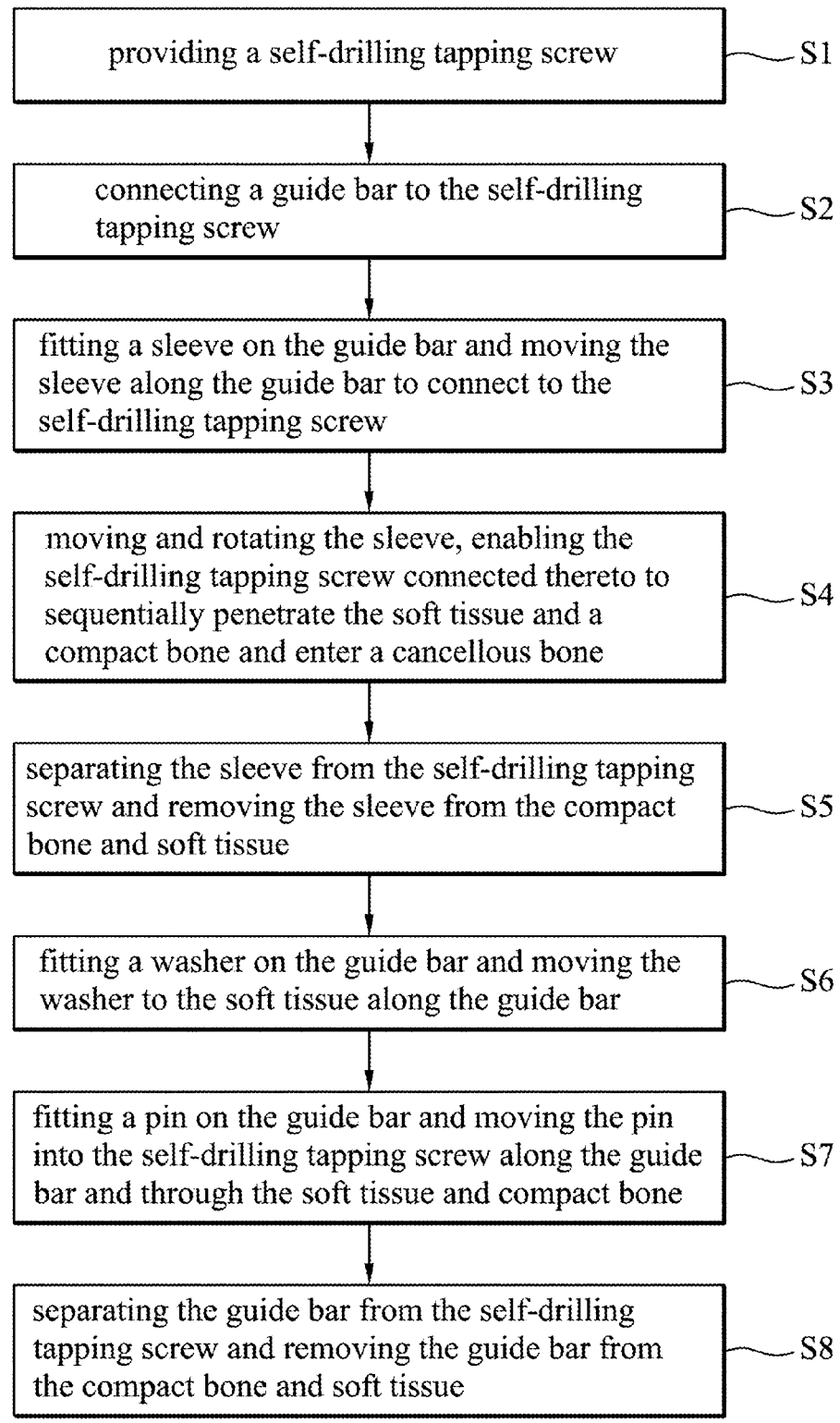
FIG. 8 is a flowchart showing a method for fixing soft tissue of the first embodiment of the invention.

Additionally, the aforementioned method for fixing soft tissue using the device 100 is shown by steps S1 to S8 in FIG. 8.

Second Embodiment

Elements corresponding to those in the first embodiment share the same reference numerals.

Figure 9:
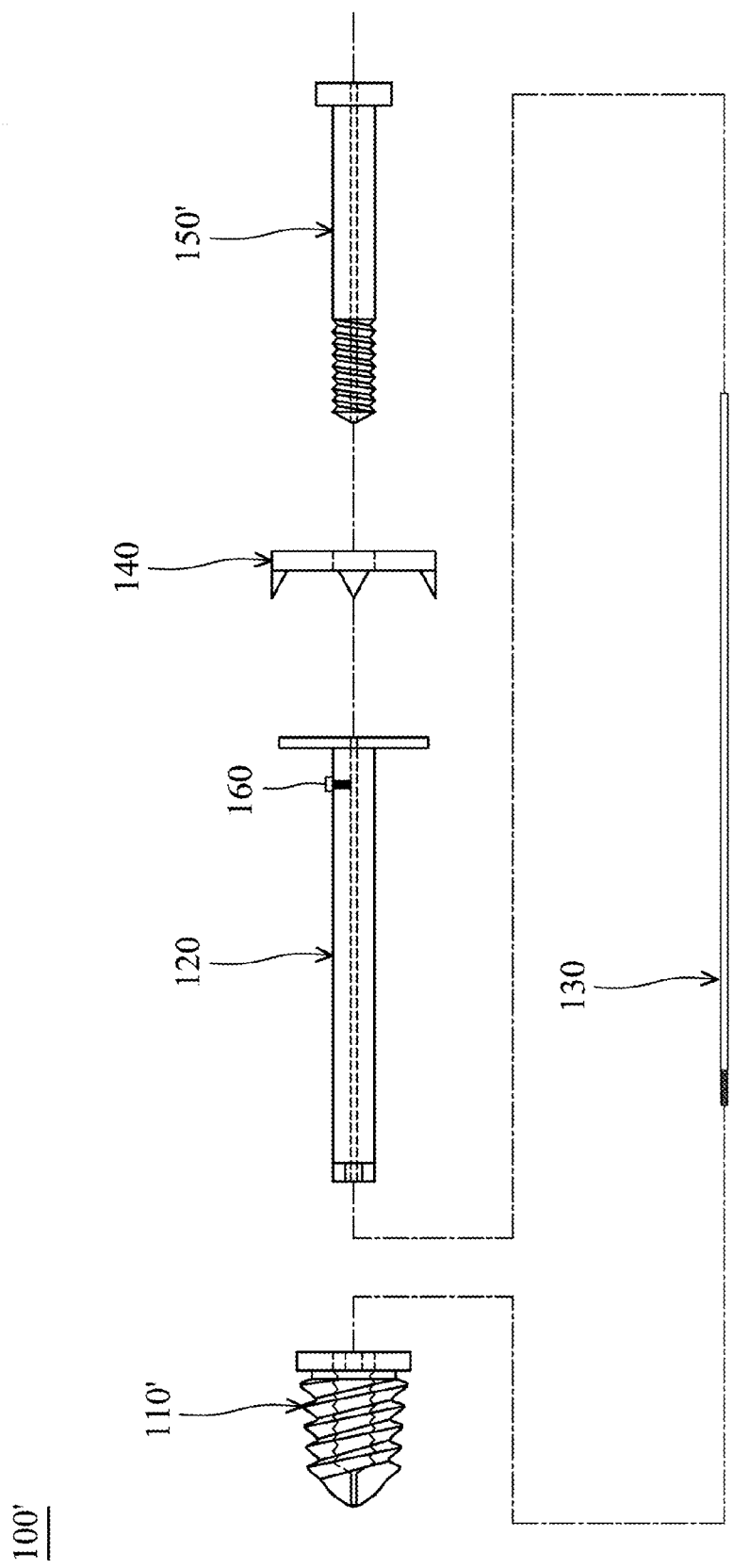
FIG. 9 is a schematic exploded view of a device for fixing soft tissue of a second embodiment of the invention.

Referring to FIG. 9, a device 100' for fixing soft tissue comprise a self-drilling tapping screw 110', a sleeve 120, a guide bar 130, a washer 140, a fixing pin 150', and an anti-slip screw 160.

Figure 10:
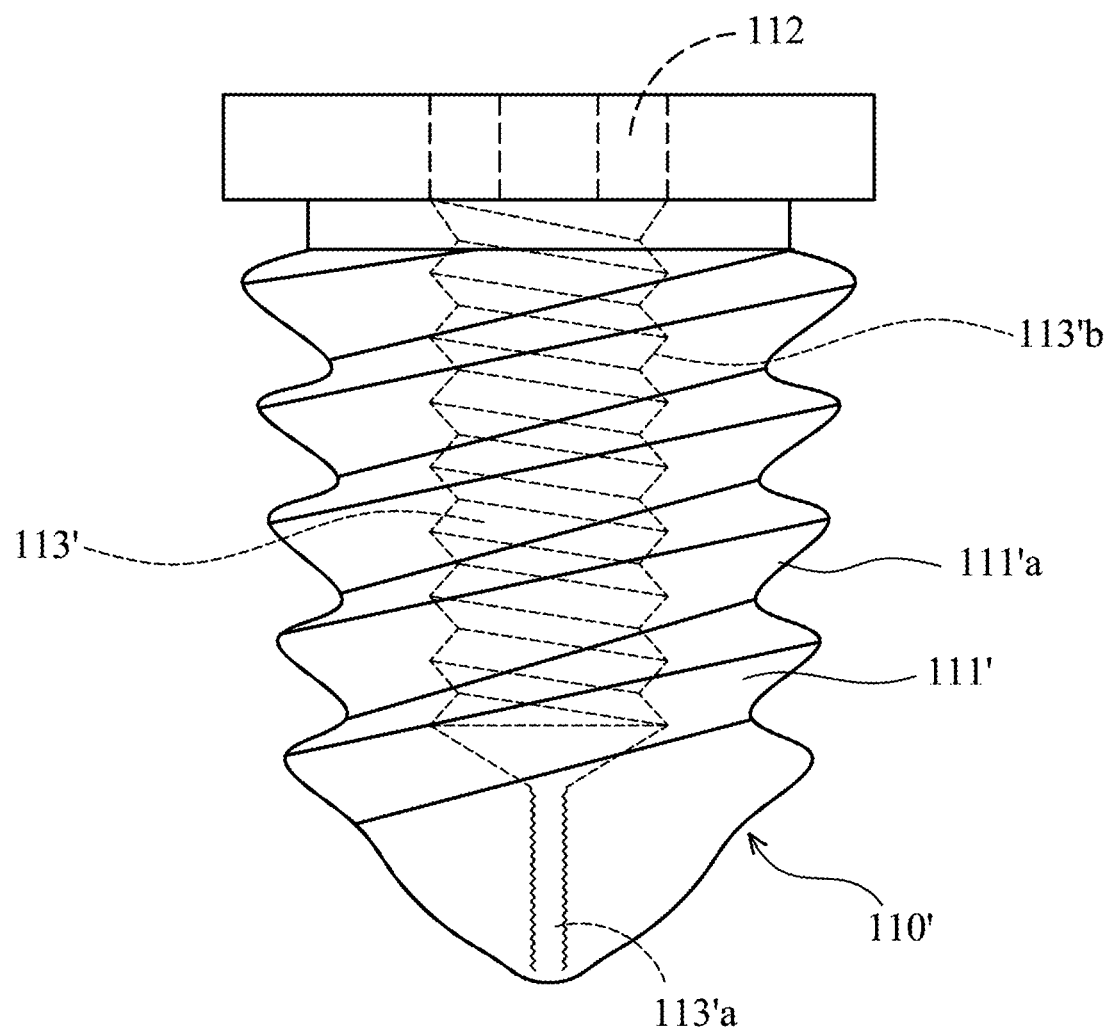
FIG. 10 is a schematic plane view of a self-drilling tapping screw of the device for fixing soft tissue of the second embodiment of the invention.

As shown in FIG. 10, the self-drilling tapping screw 110' comprises a main body 111', a first connecting portion 112, and a central hole 113'. The main body 111' comprises a first threaded portion 111'a formed on the outer surface thereof. In this embodiment, the first threaded portion 111'a is configured with outer threads. The first connecting portion 112 is connected to the main body 111'. The central hole 113' is formed in the main body 111' and comprises a second threaded portion 113'a and a fourth threaded portion 113'b. In this embodiment, the second threaded portion 113a and fourth threaded portion 113'b are configured with inner threads, and the self-drilling tapping screw 110' comprises titanium alloy, stainless steel, or biocompatible material.

Figure 11:
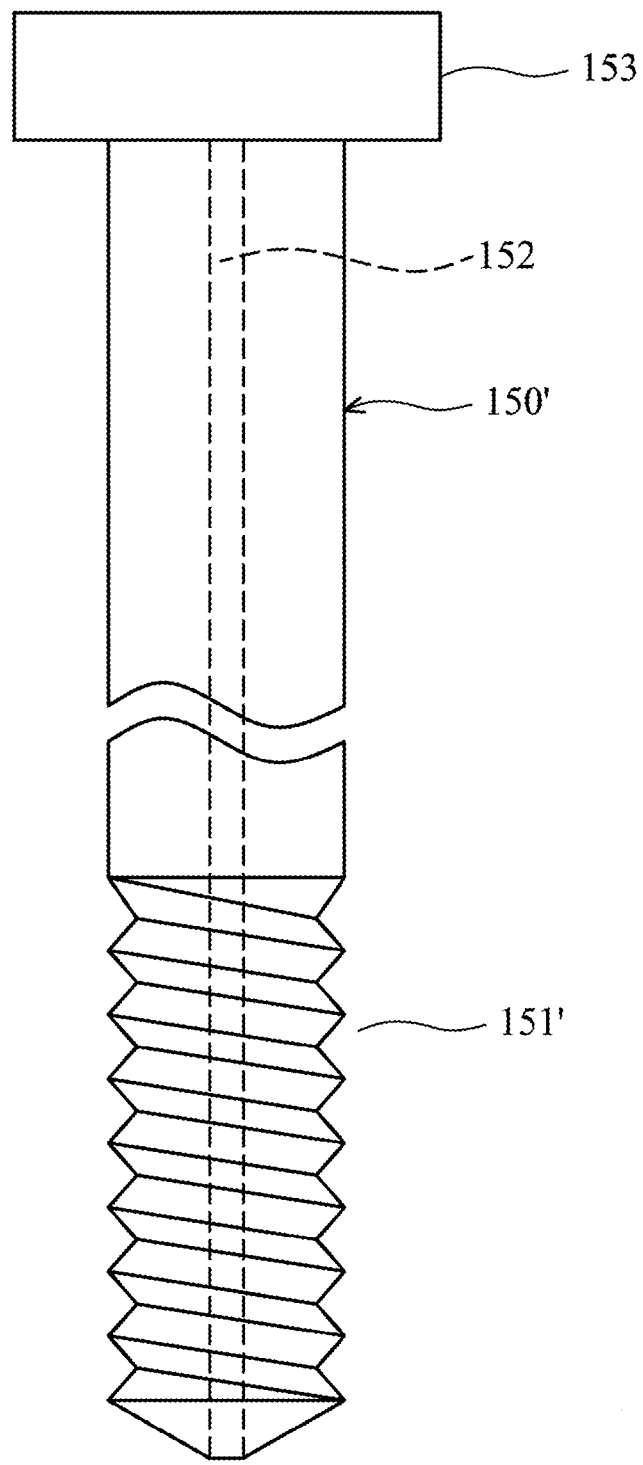
FIG. 11 is a schematic plane view of a fixing pin of the device for fixing soft tissue of the second embodiment of the invention.

As shown in FIG. 11, the fixing pin 150' comprises a fifth threaded portion 151', a third central through hole 152, and a retardant portion 153. Specifically, the fifth threaded portion 151' corresponds to the fourth threaded portion 113'b in the central hole 113' of the self-drilling tapping screw 110' and is configured with outer threads.

Moreover, the washer 140 and fixing pin 150' may comprise titanium alloy or stainless steel. Similarly, the washer 140 may be integrally formed with the fixing pin 150'.

Structure, disposition, and function of other elements in this embodiment are the same as those in the first embodiment, and explanation thereof is omitted for simplicity.

As the method for fixing soft tissue using the aforementioned device 100' is similar to that using the aforementioned device 100, the following description is directed to the difference therebetween.

Figure 12:
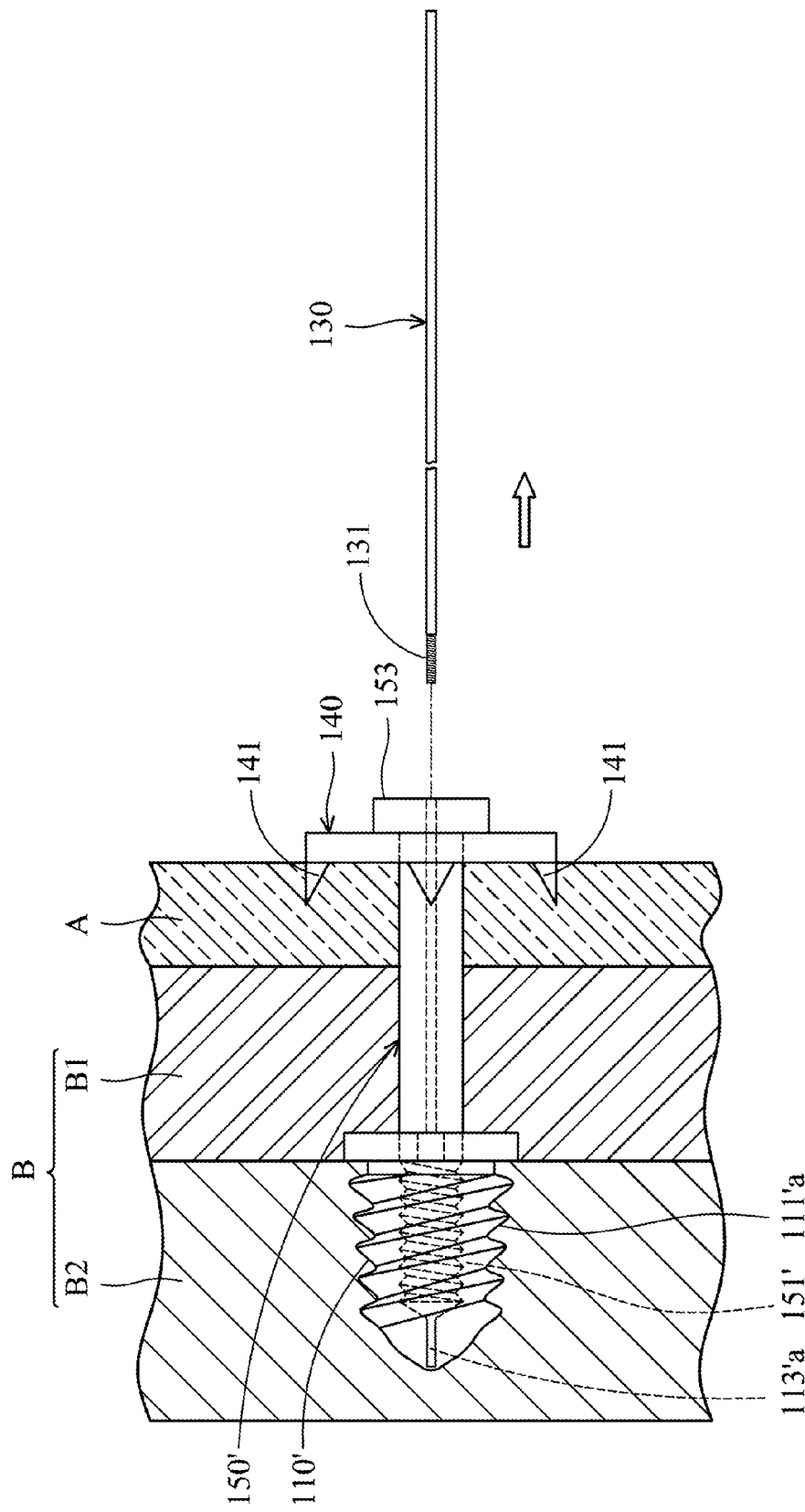
FIG. 12 is a schematic view showing operation of the device for fixing soft tissue of the second embodiment of the invention.

When a separated glenoidal labrum is fixed to a glenoidal cup of a shoulder joint by the device 100', as shown in FIG. 12, the fixing pin 150' is fixed to the self-drilling tapping screw 110'. Namely, the fifth threaded portion 151' of the fixing pin 150' engages the fourth threaded portion 113'b in the central hole 113' of the self-drilling tapping screw 110' and the retardant portion 153 thereof abuts the washer 140. Thus, the fixing pin 150' abuts between the washer 140 and the self-drilling tapping screw 110', attaching the glenoidal labrum A to the compact bone B1.

Similarly, the guide bar 130 is separated from the self-drilling tapping screw 110'. Namely, the third threaded portion 131 of the guide bar 130 is disengaged from the second threaded portion 113'a of the central hole 113' in the self-drilling tapping screw 110'. The guide bar 130 is then removed to the exterior of the glenoidal labrum A. The washer 140 is pushed into the glenoidal labrum A. At this point, the protruding splinters 141 of the washer 140 are engaged with the glenoidal labrum A, such that the glenoidal labrum A is tightly attached or fixed to the compact bone B1.

Third Embodiment

Figure 13:
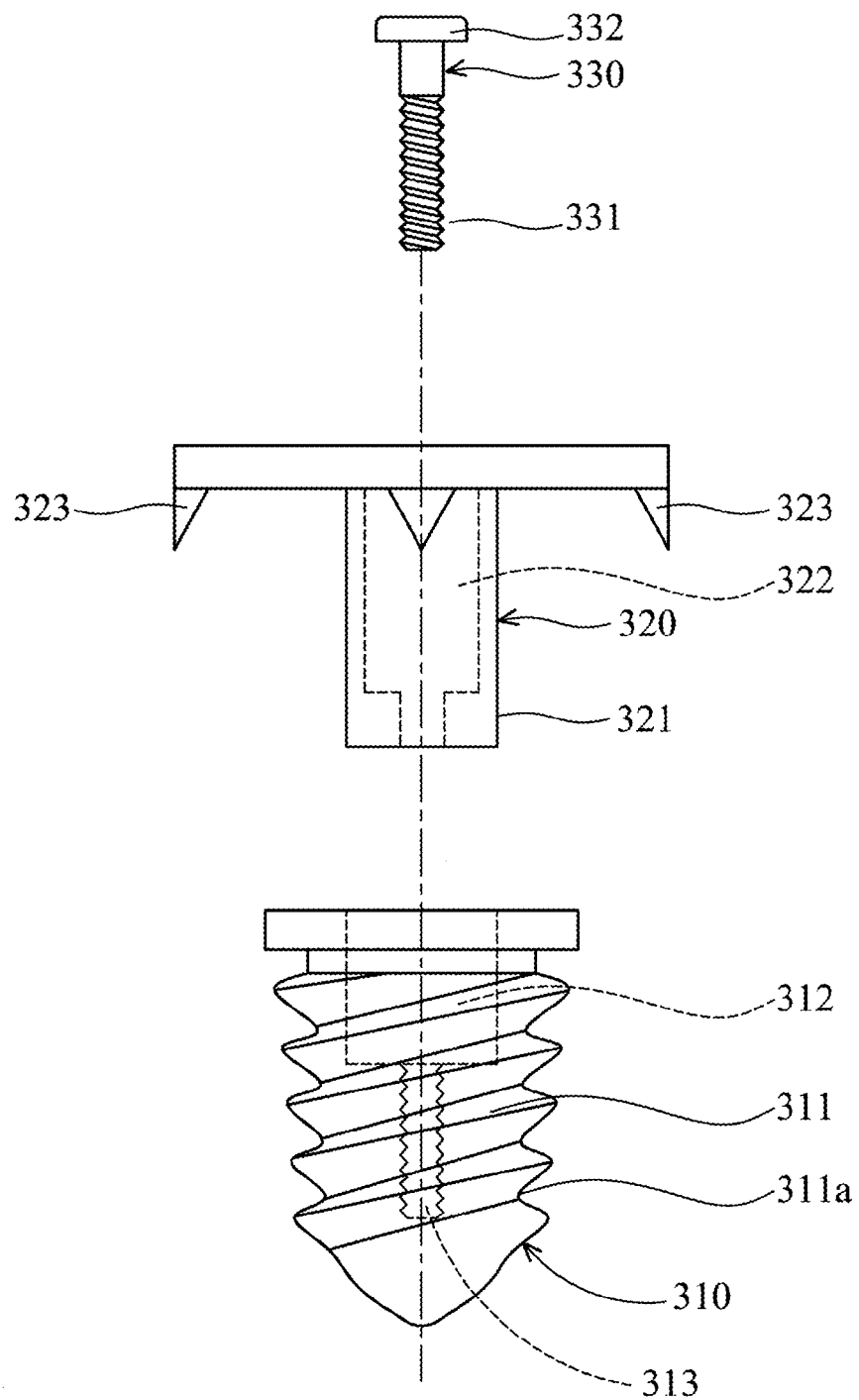
FIG. 13 is a schematic exploded view of a device for fixing soft tissue of a third embodiment of the invention.

Referring to FIG. 13, a device 100 for fixing soft tissue comprises a self-drilling tapping screw 310, a fitting member 320, and a fixing pin 330.

The self-drilling tapping screw 310 comprises a main body 311, a first hollow abutting hole 312, and a second threaded portion 313. The main body 311 comprises a first threaded portion 311a formed on the outer surface thereof. In this embodiment, the first threaded portion 311a is configured with outer threads. The first hollow abutting hole 312 is formed in the main body 311. The second threaded portion 313 is formed in the main body 311 and connected to the first hollow abutting hole 312. In this embodiment, the second threaded portion 313 is configured with inner threads, and the self-drilling tapping screw 310 may comprise titanium alloy, stainless steel, or biocompatible material.

Figure 14A:
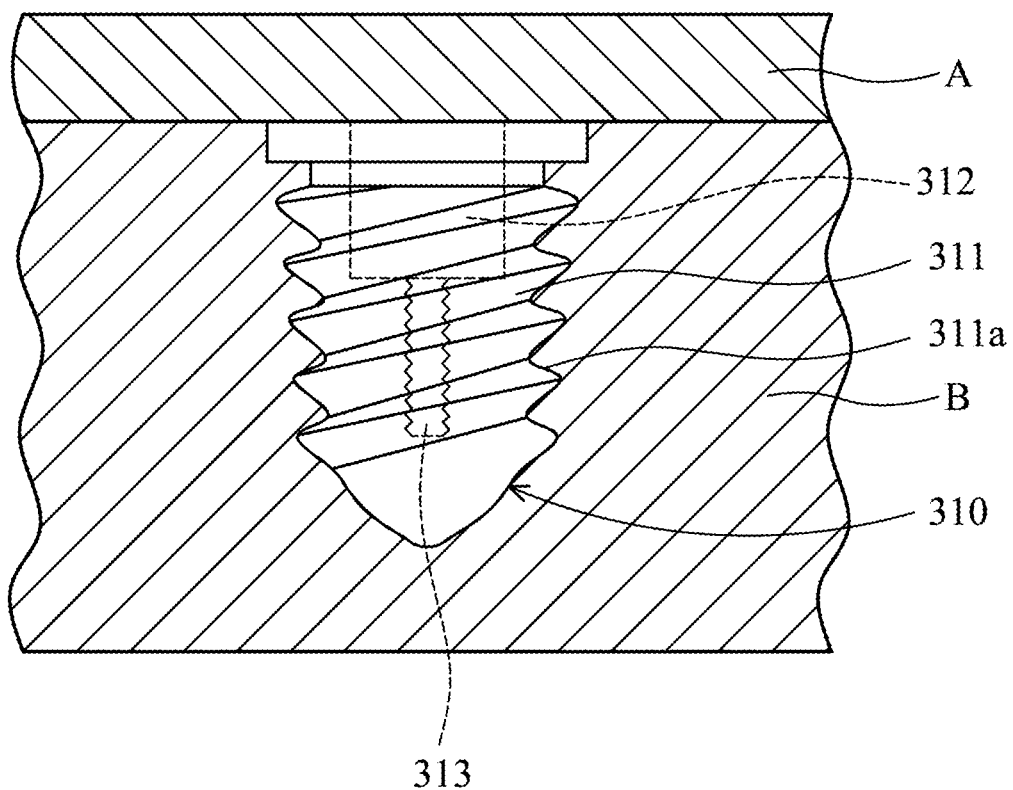
FIG. 14A is a schematic view showing operation of the device for fixing soft tissue of the third embodiment of the invention.
Figure 14B:
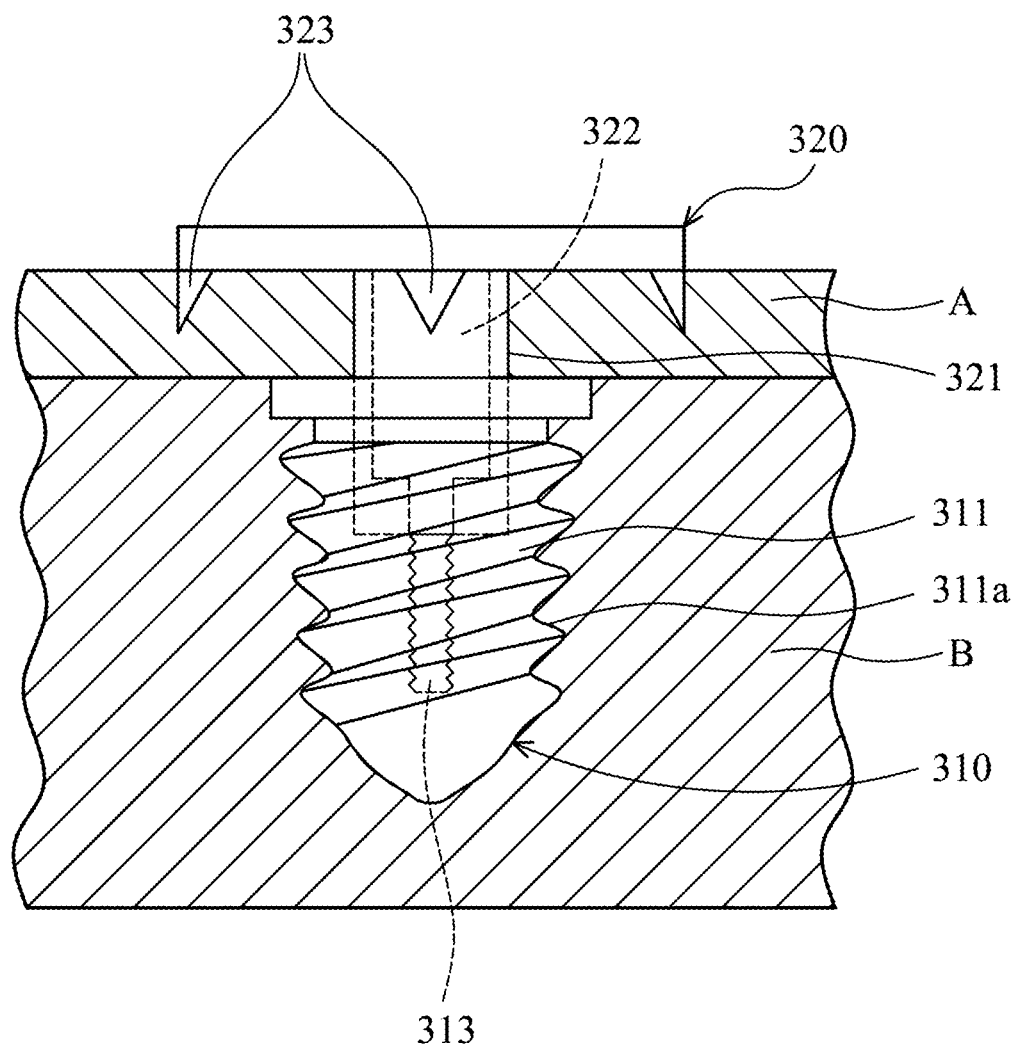
FIG. 14B is another schematic view showing operation of the device for fixing soft tissue of the third embodiment of the invention.
Figure 14C:
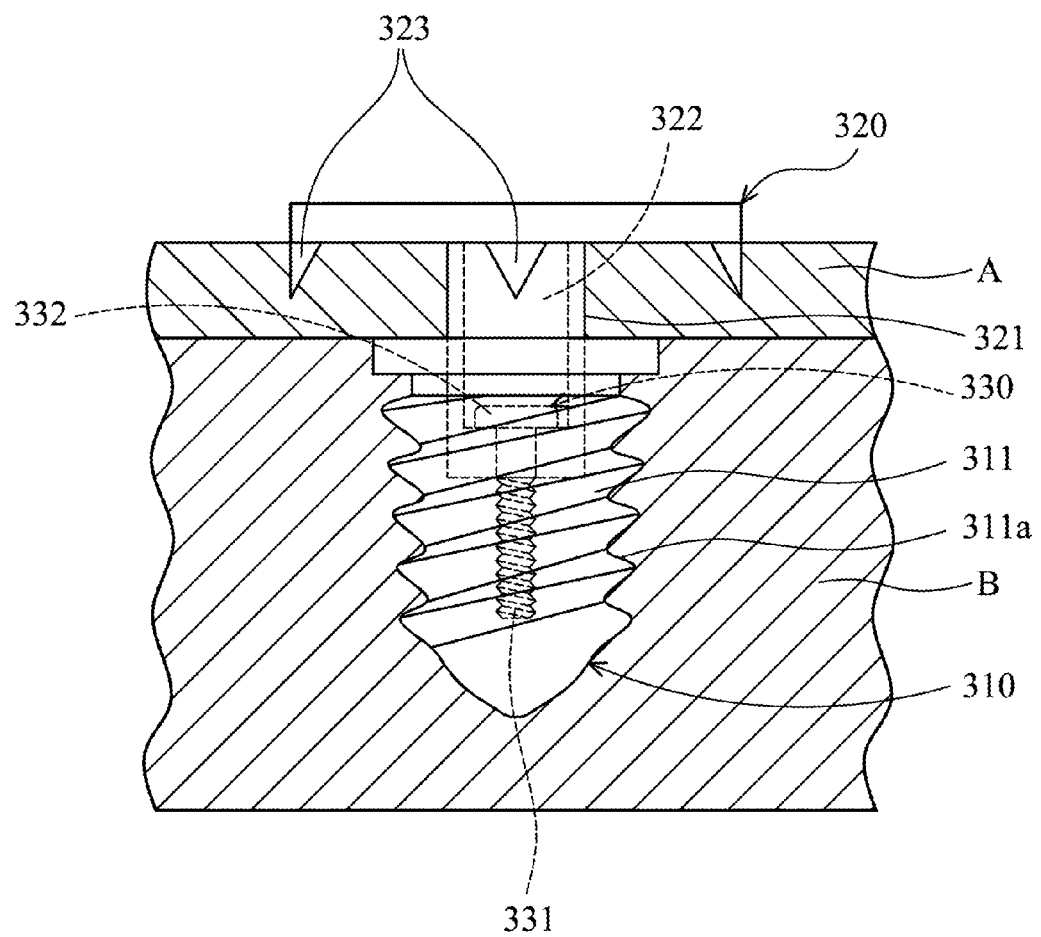
FIG. 14C is yet another schematic view showing operation of the device for fixing soft tissue of the third embodiment of the invention.

As shown in FIGS. 13, 14B, and 14C, the fitting member 320 is connected to the self-drilling tapping screw 310 and comprises a protruding abutting portion 321, a second hollow abutting portion 322, and a plurality protruding splinters 323. The protruding abutting portion 321 abuts against the first hollow abutting hole 312 of the self-drilling tapping screw 310. The second hollow abutting portion 322 is formed in the protruding abutting portion 321 and corresponds to the second threaded portion 313 of the self-drilling tapping screw 310. The protruding splinters 323 are formed on the circumference of the fitting member 320 and surround the protruding abutting portion 321. Moreover, the fitting member 320 may comprise bio-absorbable macromolecular material (such as poly lactide-glycolic acid (PLGA)) or engineering plastic.

The fixing pin 330 fits in the fitting member 320 and self-drilling tapping screw 310 and is connected to the self-drilling tapping screw 310. Specifically, the fixing pin 330 comprises a third threaded portion 331 and a retardant portion 332 connected thereto. The third threaded portion 331 engages the second threaded portion 313 of the self-drilling tapping screw 310. The retardant portion 332 abuts against the second hollow abutting portion 322 of the fitting member 320. Accordingly, when fitting in the fitting member 320 and self-drilling tapping screw 310, the fixing pin 330 is abutted between the fitting member 320 and the self-drilling tapping screw 310. Moreover, the fixing pin 330 may comprise titanium alloy, stainless steel, or biocompatible material.

The following description is directed to a method for fixing soft tissue using the aforementioned device 300. For example, a separated glenoidal labrum is fixed to a glenoidal cup of a shoulder joint.

As shown in FIG. 14A, the self-drilling tapping screw 310 is moved and rotated toward the glenoidal labrum (soft tissue) A and glenoidal cup (hard tissue) B by a tool, entering the glenoidal cup (hard tissue) B through the glenoidal labrum (soft tissue) A. At this point, the self-drilling tapping screw 310 is tightly fixed in the glenoidal cup (hard tissue) B by means of the first threaded portion 311a formed on the main body 311 thereof.

As shown in FIG. 14B, the fitting member 320 is connected to the self-drilling tapping screw 310 through the glenoidal labrum (soft tissue) A, such that the glenoidal labrum (soft tissue) A is between the self-drilling tapping screw 310 and the fitting member 320. Here, the protruding abutting portion 321 of the fitting member 320 abuts against the first hollow abutting hole 312 of the self-drilling tapping screw 310, and the protruding splinters 323 thereof are engaged with the glenoidal labrum (soft tissue) A.

As shown in FIG. 14C, the fixing pin 330 is fit in the fitting member 320 and self-drilling tapping screw 310 and is connected to the self-drilling tapping screw 310. Here, the fixing pin 330 is abutted between the fitting member 320 and the self-drilling tapping screw 310. Namely, the third threaded portion 331 of the fixing pin 330 engages the second threaded portion 313 of the self-drilling tapping screw 310, and the retardant portion 332 of the fixing pin 330 abuts against the second hollow abutting portion 322 of the fitting member 320. Accordingly, the glenoidal labrum (soft tissue) A is tightly attached to the glenoidal cup (hard tissue) B.

Figure 15:
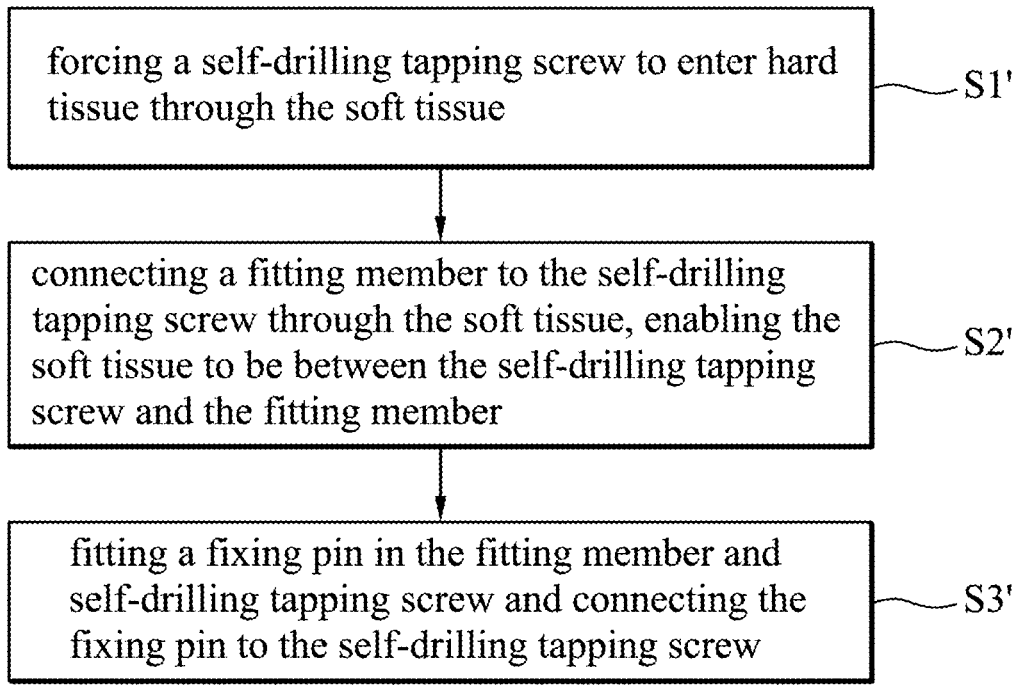
FIG. 15 is a flowchart showing a method for fixing soft tissue of the third embodiment of the invention.

Additionally, the aforementioned method for fixing soft tissue using the device 300 is shown by steps S1' to S3' in FIG. 15.

In conclusion, when the separated glenoidal labrum (soft tissue) is re-fixed to the glenoidal cup (hard tissue) of the shoulder joint by the disclosed device and method, no suture is required, thus reducing surgical complexity and time. Moreover, the disclosed device and method provide superior attachment or fixing of the glenoidal labrum (soft tissue), facilitating reconstruction and regeneration thereof.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A device for fixing soft tissue, comprising:
a self-drilling tapping screw;
a guide bar connected to the self-drilling tapping screw;
a sleeve comprising a first central through hole and configured to be detachably connected to the self-drilling tapping screw to move and rotate the self-drilling tapping screw, wherein the sleeve is fit on the guide bar via the first central through hole;
a washer comprising a second central through hole; and
a fixing pin comprising a third central through hole and fit in the washer through the second central through hole, wherein the fixing pin is configured to fit on the guide bar via the third central through hole and connect to the self-drilling tapping screw after the sleeve is detached so as to abut the washer and the self-drilling tapping screw;
wherein the guide bar is detachable from the self-drilling tapping screw and the fixing pin.

2. The device as claimed in claim 1, wherein the self-drilling tapping screw comprises a main body and a first threaded portion formed on the outer surface thereof.

3. The device as claimed in claim 2, wherein the self-drilling tapping screw further comprises a first connecting portion connected to the main body, and the sleeve comprises a second connecting portion detachably connected to the first connecting portion.

4. The device as claimed in claim 3, wherein the first and second connecting portions are complementary.

5. The device as claimed in claim 2, wherein the self-drilling tapping screw further comprises a central hole formed in the main body, and the guide bar is detachably disposed in the central hole.

6. The device as claimed in claim 5, wherein the central hole comprises a second threaded portion, and the guide bar comprises a third threaded portion engaging the second threaded portion.

7. The device as claimed in claim 2, wherein the self-drilling tapping screw further comprises a central hole formed in the main body, and the fixing pin is disposed in the central hole.

8. The device as claimed in claim 7, wherein the central hole comprises at least one first engaging portion, and the fixing pin comprises at least one second engaging portion engaging the first engaging portion.

9. The device as claimed in claim 8, wherein the first and second engaging portions are complementary.

10. The device as claimed in claim 7, wherein the central hole comprises a fourth threaded portion, and the fixing pin comprises a fifth threaded portion engaging the fourth threaded portion.

11. The device as claimed in claim 1, wherein the sleeve comprises a first central through hole in which the guide bar is detachably fit.

12. The device as claimed in claim 11, further comprising an anti-slip screw detachably fit in the sleeve and movably protruding into the first central through hole, abutting and fixing the guide bar.

13. The device as claimed in claim 1, wherein the washer comprises at least one protruding splinter formed on the circumference thereof.

14. The device as claimed in claim 1, wherein the fixing pin further comprises a retardant portion abutting the washer.

15. The device as claimed in claim 1, wherein the self-drilling tapping screw, washer, and fixing pin comprise titanium alloy, stainless steel, or biocompatible material.

16. The device as claimed in claim 1, wherein the washer and fixing pin comprise bio-absorbable macromolecular material.

17. The device as claimed in claim 1, wherein the washer is integrally formed with the fixing pin.

18. A device for fixing soft tissue, comprising:
a self-drilling tapping screw comprising a main body, a first threaded portion formed on the outer surface thereof, a first hollow abutting hole formed in the main body, and a second threaded portion formed in the main body and connected to an abutting surface of the first hollow abutting hole;
a fitting member, connected to the self-drilling tapping screw, comprising a protruding abutting portion fit into the first hollow abutting hole and abutting against the abutting surface of the first hollow abutting hole, a second hollow abutting hole formed in the protruding abutting portion, and at least one protruding splinter formed on the circumference thereof and surrounding the protruding abutting portion, wherein the second hollow abutting hole is aligned with the second threaded portion; and
a fixing pin fit in the second hollow abutting hole of the fitting member and into the self-drilling tapping screw and connected to the second threaded portion of the self-drilling tapping screw, wherein the fixing pin is abutted between the fitting member and the self-drilling tapping screw.

19. The device as claimed in claim 18, wherein the fixing pin comprises a third threaded portion and a retardant portion, the third threaded portion is connected to the retardant portion and engages the second threaded portion, and the retardant portion abuts against the second hollow abutting hole.

20. The device as claimed in claim 18, wherein the self-drilling tapping screw and fixing pin comprise titanium alloy, stainless steel, or biocompatible material, and the fitting member comprises bio-absorbable macromolecular material.

21. The device as claimed in claim 18, wherein the fitting member comprises poly lactide-glycolic acid (PLGA) or engineering plastic.

* * * * *

UNITED STATES PATENT AND TRADEMARK OFFICE
CERTIFICATE OF CORRECTION

PATENT NO.         : 8,435,271 B2
APPLICATION NO.    : 13/231924
DATED              : May 7, 2013
INVENTOR(S)        : Ching-Chuan Jiang et al.

It is certified that error appears in the above-identified patent and that said Letters Patent is hereby corrected as shown below:

On the Title page, Item (73) Assignee(s) should read:
Industrial Technology Research Institute, Hsinchu (TW)
National Taiwan University Hospital, Taipei City (TW)

Signed and Sealed this
Twenty-ninth Day of April, 2014

Michelle K. Lee
*Deputy Director of the United States Patent and Trademark Office*